United States Patent
Colijn et al.

(10) Patent No.: US 10,562,012 B2
(45) Date of Patent: Feb. 18, 2020

(54) PROCESS FOR THE PREPARATION OF A CATALYST AND A PROCESS FOR PRODUCING GLYCOLS USING THE CATALYST

(71) Applicant: SHELL OIL COMPANY, Houston, TX (US)

(72) Inventors: Hendrik Albertus Colijn, Amsterdam (NL); Dionysius Jacobus Maria De Vlieger, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/092,052

(22) PCT Filed: Apr. 7, 2017

(86) PCT No.: PCT/EP2017/058465
§ 371 (c)(1),
(2) Date: Oct. 8, 2018

(87) PCT Pub. No.: WO2017/178391
PCT Pub. Date: Oct. 19, 2017

(65) Prior Publication Data
US 2019/0111413 A1    Apr. 18, 2019

(30) Foreign Application Priority Data
Apr. 11, 2016  (EP) .................................... 16164685

(51) Int. Cl.
| | | |
|---|---|---|
| C07C 29/00 | (2006.01) | |
| B01J 23/00 | (2006.01) | |
| B01J 23/30 | (2006.01) | |
| B01J 37/18 | (2006.01) | |
| B01J 23/36 | (2006.01) | |
| B01J 23/42 | (2006.01) | |
| B01J 23/44 | (2006.01) | |
| B01J 23/46 | (2006.01) | |
| B01J 23/72 | (2006.01) | |
| B01J 23/75 | (2006.01) | |
| B01J 23/755 | (2006.01) | |
| B01J 37/02 | (2006.01) | |
| C07C 29/132 | (2006.01) | |
| C07C 29/60 | (2006.01) | |
| C07C 29/16 | (2006.01) | |
| C07C 31/20 | (2006.01) | |

(52) U.S. Cl.
CPC ............... *B01J 23/30* (2013.01); *B01J 23/36* (2013.01); *B01J 23/42* (2013.01); *B01J 23/44* (2013.01); *B01J 23/462* (2013.01); *B01J 23/468* (2013.01); *B01J 23/72* (2013.01); *B01J 23/75* (2013.01); *B01J 23/755* (2013.01); *B01J 37/0201* (2013.01); *B01J 37/18* (2013.01); *C07C 29/132* (2013.01); *C07C 29/16* (2013.01); *C07C 29/60* (2013.01); *C07C 31/202* (2013.01); *C07C 31/205* (2013.01); *Y02P 20/52* (2015.11)

(58) Field of Classification Search
CPC ........ C07C 29/132; C07C 29/16; B01J 23/30; B01J 23/42; B01J 23/44; B01J 23/462
See application file for complete search history.

(56) References Cited

U.S. PATENT DOCUMENTS

| 4,476,331 A | 10/1984 | Dubeck et al. |
| 4,503,274 A | 3/1985 | Arena |
| 2012/0172633 A1 | 7/2012 | Zhang et al. |

FOREIGN PATENT DOCUMENTS

WO    2015028398 A1    3/2015

OTHER PUBLICATIONS

International Search Report and Written Opinion received for PCT Patent Application No. PCT/EP2017/058465, dated May 12, 2017, 8 pages.
Ji et al., "Direct Catalytic Conversion of Cellulose into Ethylene Glycol Using Nickel-Promoted Tungsten Carbide Catalysts", Angewandte Chemie Int. Ed., vol. 47, Issue 44, Oct. 20, 2008, pp. 8510-8513.

*Primary Examiner* — Sikarl A Witherspoon

(57) ABSTRACT

A process for the preparation of a catalyst composition for catalysing hydrogenation and hydrogenolysis reactions wherein, (a) a carbon support is contacted with a catalyst precursor solution comprising at least one element from groups 7, 8, 9, 10 and 11 of 5 the periodic table to form a metal impregnated carbon; (b) the metal impregnated carbon is dried at a temperature of no greater than 400° C. and placed in a reactor vessel; (c) the reactor vessel is sealed; and (d) the metal impregnated carbon is treated in the reactor 10 vessel in an atmosphere comprising hydrogen at a temperature of from 25° C. to 350 ° C.

8 Claims, No Drawings

PROCESS FOR THE PREPARATION OF A CATALYST AND A PROCESS FOR PRODUCING GLYCOLS USING THE CATALYST

CROSS REFERENCE TO RELATED APPLICATIONS

This is a national stage application of International Application No. PCT/EP2017/058465, filed 7 Apr. 2017, which claims benefit of priority to European Application No. 16164685.6, filed 11 Apr. 2016.

FIELD OF THE INVENTION

The present invention relates to a process for preparing a catalyst composition and to a process that uses the catalyst composition for producing glycols from saccharide-containing feedstock under aqueous conditions.

BACKGROUND OF THE INVENTION

Glycols such as mono-ethylene glycol (MEG), mono-propylene glycol (MPG) and 1,2-butanediol (1,2-BDO) are valuable materials with a multitude of commercial applications, e.g. as heat transfer media, antifreeze, and precursors to polymers, such as PET or polyester. Ethylene and propylene glycols are typically made on an industrial scale by hydrolysis of the corresponding alkylene oxides, which are the oxidation products of ethylene and propylene, produced from fossil fuels.

In recent years, increased efforts have focussed on producing chemicals, including glycols, from non-petrochemical renewable feedstocks, such as sugar-based materials. The conversion of sugars to glycols can be seen as an efficient use of the starting materials with the oxygen atoms remaining intact in the desired product.

Current methods for the conversion of saccharides to glycols revolve around a two-step process of retro-aldol fragmentation and hydrogenation, as described in Angew, Chem. Int. Ed. 2008, 47, 8510-8513. Sponge metal catalysts such as Raney nickel are often used as the hydrogenation catalyst in such processes. Some amounts of leaching may occur with these catalysts and such leaching can lead to the presence of metal in the product, or could lead to catalyst deactivation.

WO2015028398 describes a continuous process for the conversion of a saccharide-containing feedstock into glycols. In this process the saccharide-containing feedstock is contacted in a single reactor with two catalysts, hydrogen and a solvent. For example, a solution of glucose in water is contacted with a W/Ni/Pt on zirconia catalyst and a Ru on silica catalyst in the presence of hydrogen. The former catalyses the initial conversion of the saccharide-containing feedstock into retro-aldol fragments (e.g. glycolaldehyde and hydroxyacetone), and the latter coverts such fragments to MEG, MPG and 1,2-BDO. The temperature of the reaction is typically 195° C. and the absolute pressure is typically around 7.5 MPa, however, often the reaction temperature may need to be in the region of around 220° C. to 240° C. to drive the initial conversion of the saccharide-containing feedstock into retro-aldol fragments.

U.S. Pat. No. 4,503,274 discloses the inorganic oxide catalyst supports alpha-alumina, theta-alumina, titanated alumina and titania, and describes hydrogenating a carbohydrate in aqueous solution to its polyols at a preferred temperature range of from about 105° C. to 130° C. The catalyst used in such reaction is a catalyst consisting essentially of zerovalent ruthenium dispersed on theta-alumina support, where the zerovalent ruthenium is produced by the reduction of the impregnated ruthenium on the on theta-alumina support with hydrogen at a temperature from about 100° C. to about 300° C.

As described by its inventors, the catalyst of U.S. Pat. No. 4,503,274 appears to have better hydrothermal stability than its prior art, in particular when an aqueous solution of carbohydrates is treated with hydrogen at hydrogenation conditions of a preferred reaction temperature of 105 to 130° C. However, the present inventors have observed that in the hotter aqueous conditions which they use (which may be up to 250° C.) for the production of glycols from saccharide-containing feedstock, such catalyst compositions are not hydrothermally stable, probably due to the inorganic oxide catalyst supports. For example, such catalyst supports may undergo phase changes or growth of crystallites, or may begin to dissolve. This can detrimentally affect catalytic performance, leading to lower glycol yields, and the need to change the catalyst more frequently. This can also lead to system instability such that reaction conditions may need to be changed to maintain catalyst performance. Additionally, dissolution of catalyst components can lead to the presence of impurities in the glycol process.

Typically, a first step of the known processes for the preparation of supported catalysts is the impregnation of catalyst supports with the ionic form of catalytically active metal(s) of choice. A common practice after impregnation is to dry the support to remove the solvent used in the impregnation step. After this, commonly a heat treatment step, in either an oxygen- or a hydrogen-containing atmosphere is carried out. Following the treatment by any one of these gasses, further steps are commonly required before the catalyst can be ready for its intended use. If oxygen-treated, typically a further step of reduction is required to convert the impregnated metal ion to its catalytically active metallic state. If hydrogen-treated, the reduced metal particles usually become pyrophoric, so they then require a further step of passivation before they can be exposed to an oxygen containing atmosphere, such as air. During passivation, a protective surface coating, usually comprising the metal's oxide, is formed by subjecting the metal particles to a low concentration of oxygen in a temperature- and oxygen concentration controlled manner known in the art. Following the passivation step, a second reduction step needs to be carried out before the catalyst can be ready for its intended use.

Both these gas treatments affect the resultant catalyst's activity profile and physical properties differently, with each having its own disadvantages. Some of the disadvantages of the oxygen-treatment are, for example, the vulnerability of supports comprising carbon to burn during the oxygen-treatment, or the promotion of particle size growth of the impregnated metal by sintering. In the case of hydrogen-treatment, the main disadvantage is the formation of the pyrophoric metal particles, which without the passivation step would begin to heat up in the presence of an oxygen containing atmosphere, such as air, and lead to metal particle growth.

A further disadvantage of the known processes for the preparation of supported catalysts is the lack of hydrothermal stability of the catalyst compositions that such support impregnation processes produce. Such hydrothermal instability can be seen, in particular, when such a catalyst composition is used under the conditions of the continuous conversion of a saccharide-containing feedstock into glycols described herein.

Overall, prior art support impregnation processes are complicated by their complexity, as they comprise numerous and alternative process steps, and their resultant catalyst products are not hydrothermally stable and active under some conditions. Therefore, a process which reduces the complexity and the number of steps of the impregnation process, and one that produces a catalyst that is hydrothermally stable and active across a wider range of conditions would be desirable.

Therefore the present inventors have sought to obtain a hydrothermally stable catalyst composition suitable for one or more steps of the continuous conversion of a saccharide-containing feedstock into glycols, and have discovered that the catalyst composition making process described herein not only makes a hydrothermally stable active catalyst for the conversion of a saccharide-containing feedstock into glycols, but also one which is quicker and easier to prepare compared to the processes of the prior art.

SUMMARY OF THE INVENTION

Accordingly, the present invention provides a process for the preparation of a catalyst composition for catalysing hydrogenation and hydrogenolysis reactions wherein, (a) a carbon support is contacted with a catalyst precursor solution comprising at least one element from groups 7, 8, 9, 10 and 11 of the periodic table to form a metal impregnated carbon; (b) the metal impregnated carbon is dried at a temperature of no greater than 400° C. and placed in a reactor vessel; (c) the reactor vessel is sealed; and (d) the metal impregnated carbon is treated in the sealed reactor vessel in an atmosphere comprising hydrogen at a temperature of from 25° C. to 350° C. to form an activated catalyst composition.

The present invention also provides a process for the production of glycols comprising the step of preparing a catalyst composition in accordance with the abovementioned process, and whilst the catalyst composition remains inside the reactor vessel in an atmosphere comprising hydrogen, supplying to the reactor vessel a saccharide-containing feedstock, a retro-aldol catalyst composition a solvent and further hydrogen.

The present inventors have found that the carbon supported catalyst composition prepared according to the process of the invention not only produces a hydrothermally stable and active catalyst, but also provides a quicker and easier way to produce such catalyst, compared to the prior art.

DETAILED DESCRIPTION OF THE INVENTION

The present invention provides a process for the preparation of a catalyst composition for catalysing hydrogenation and hydrogenolysis reactions. In such a preparation process, a carbon support is contacted with a catalyst precursor solution comprising at least one element from groups 7, 8, 9, 10 and 11 of the periodic table to form a metal impregnated carbon.

In relation to this invention, 'retro-aldol fragmentation' includes a process where sugar molecules are cleaved in to retro-aldol fragments, 'hydrogenolyis' includes a process in which hydrogen is used to cleave larger hydrocarbon molecules (such as sugar alcohols) into two smaller fragments, and 'hydrogenation' includes the addition of hydrogen atoms to carbonyl containing components to form hydroxyl groups (e.g. to retro-aldol fragments, such as during the conversion of glycolaldehyde and hydroxyacetone to ethylene glycol and propylene glycol).

The carbon support may be activated carbon, carbon black, graphite, graphene based or structure carbons such as carbon nanotubes and carbon nanofibers. Activated carbon is a form of carbon processed to have high surface area or microporosity. One gram of activated carbon may have a surface area in excess of 500 $m^2$. Activated carbon may be produced from materials of biological origin such as peat, wood, nutshells, coconut husk or coir, as well as from mineralised matter such as coal and lignite. Such materials are subjected to either 'physical' reactivation, and/or to 'chemical' reactivation, both as known in the art. The 'activation' of the carbon is a result of either exposure to an oxidising atmosphere (during physical reactivation,) or to an acid, strong base or a salt followed by carbonisation (during chemical reactivation). Whichever way it is produced, the high microporosity makes activated carbon an excellent candidate for its use as a catalyst support, as its ability to absorb, bind or interact with other compounds is enhanced by its activated high surface area. Carbon black on the other hand is produced by the incomplete combustion or thermal decomposition of gaseous or liquid hydrocarbons. It typically has a lower surface area than activated carbon. Depending of its production method, the carbon support of any of the above-mentioned carbon types may have hydrophilic or hydrophobic surface properties. Suitably, the activated carbon, the carbon black, graphite, the carbon nanotubes or the carbon nanofibers that may be used as the carbon support can be all sourced from commercial suppliers known to the skilled person.

A catalyst precursor solution, used to make a metal impregnated carbon, comprises at least one element from groups 7, 8, 9, 10 and 11 of the periodic table. The at least one element from groups 7, 8, 9, 10 and 11 of the periodic table may be suitably selected from a group consisting of ruthenium, cobalt, nickel, palladium, platinum, iridium, rhenium and copper. Suitably the catalyst precursor solution may comprise a single such metal, or suitably a combination of at least one other metals from said groups of the periodic table. Suitably the catalyst precursor solution comprises ruthenium. Suitably, the combination of at least one other metals from said groups of the periodic table may be, but not restricted to, for example, ruthenium and palladium or ruthenium and platinum, ruthenium and rhenium, and platinum and nickel.

To prepare the catalyst precursor solution, suitably a salt or a complex of the abovementioned metal(s) is selected. The salt or complex may comprise anions such as, but not limited to, nitrate, chloride, nitrosyl nitrate, acetylacetonate. The salt or the complex needs to be soluble in the solvent of choice, such that a sufficient amount of the at least one element from groups 7, 8, 9, 10 and 11 of the periodic table is present in a dissolved form in the catalyst precursor solution for impregnating the carbon support. The meaning of 'sufficient amount' is discussed below.

The solvent used to make the catalyst precursor solution of the abovementioned salts or complexes may be water, or may be organic compounds such as, but not limited to, $C_1$ to $C_5$ primary alcohols and ketones such as acetone, or mixtures thereof.

The choice of the solvent used depends not only on whether said salt or complex in question is soluble in a given solvent, but also on whether the chosen carbon support has a hydrophilic or a hydrophobic surface property. For example, a suitable combination is, ruthenium nitrosyl nitrate dissolved in water to impregnate a carbon support with hydrophilic surface properties. An alternative is, for example, ruthenium acetylacetonate dissolved in acetone to impregnate a carbon support with hydrophobic surface properties, such as graphite.

To prepare the catalyst precursor solution, the total amount of the abovementioned metal in said solution needs to be known; such amount being referred to herein as a/the 'sufficient amount'. The sufficient amount is dependent on the amount of carbon support to be impregnated, such that, after contacting the carbon support with the catalyst precursor solution the total weight percentage of the at least one element from groups 7, 8, 9, 10 and 11 of the periodic table impregnated on the carbon support compared to the total weight of the resultant catalyst is preferably at least 0.2% wt. metal, more preferably at least 0.5% wt. metal and even more preferably at least 1% wt. metal, most preferably at least 2% wt. metal, and preferably at most 10% wt. metal, more preferably at most 7% wt. metal and even more preferably at most 5% wt. metal.

With the knowledge of the 'sufficient amount', a volume of the catalyst precursor solution is prepared. The 'sufficient amount' of the catalyst precursor solution is contacted with a predetermined amount of the carbon support, and suitably, a brief mixing step is then performed to enhance the even contact of the catalyst precursor solution with the carbon support. Suitably, during and immediately after the brief mixing step, the catalyst precursor solution becomes evenly distributed over the carbon surface area, and as the solvent is removed by drying, the dissolved metal in the catalyst precursor solution begins to impregnate on the carbon support. The principles underlying such absorption/deposition/impregnation process, otherwise known as incipient wetness impregnation, is known to the skilled person. Suitably, other methods of metal absorption/deposition/impregnation that are known to the skilled person may be also used. At the end of these steps a metal impregnated carbon is formed.

Suitably, the metal impregnated carbon is placed in an open container, and to dry the metal impregnated carbon, the container is placed in an oven. Suitably, the shape and size of the open container can be determined by the skilled person according the amount of metal impregnated carbon to be dried. Suitably, the type of oven, or a drying apparatus, can be determined by the skilled person.

The metal impregnated carbon is dried at a temperature of no greater than 400° C., so that the processes of calcining and metal sintering, known to the skilled person, are avoided. Preferably drying temperature is at most 300° C., more preferably at most 225° C., even more preferably at most 150° C., and most preferably at most 100° C. Preferably drying temperature is at least room temperature, more preferably at least 30° C., even more preferably at least 50° C., and most preferably at least 70° C. Suitably, if the drying temperature is at most 300° C., typically the drying time may be no longer than 30 minutes. Suitably, if the drying temperature is at most 225° C., typically the drying time may be no longer than 2 hours. Suitably, if the drying temperature is at most 150° C. or less, typically the drying time may be overnight. If for example, the catalyst precursor solution comprised a water-soluble ruthenium salt or complex of ruthenium and a hydrophilic carbon support is selected, suitably the drying temperature is from about 60° C. to about 80° C., and the drying time is overnight. Suitably, the atmospheric composition in the oven during the drying step is the same as ambient atmospheric composition.

Without being bound to any particular theory, it is thought that during the contact step, the metal ions of the at least one element from groups 7, 8, 9, 10 and 11 of the periodic table gains access to the surface of the carbon support, including to the pores of the carbon support. As the drying progress, the concentration of the dissolved salt or complex will reach saturation, and metal ions will begin to deposit on the carbon support, and impregnate it. Finally when all of the solvent has evaporated, the carbon support will be impregnated with the at least one element from groups 7, 8, 9, 10 and 11 of the periodic table, which is referred to herein as a metal impregnated carbon.

Following the drying step, a catalyst activation step is carried out to stabilise the metal particles and to enhance their catalytic activity, by placing the dried metal impregnated carbon in a sealable reactor vessel, which is intended to be used, for example, for the hydrogenation step in the glycol production process described herein, and/or for the hydrogenolysis of sugar alcohols to smaller components. The dried metal impregnated carbon is treated in said reactor vessel, with the reactor vessel sealed, in an atmosphere comprising hydrogen to reduce the at least one element from groups 7, 8, 9, 10 and 11 of the periodic table on the carbon support to its/their metallic state.

Based on the volume of the reactor vessel, the atmosphere comprising hydrogen preferably contains less than 4% vol. oxygen, more preferably less than 1% vol. oxygen, even more preferably less than 0.1% vol. oxygen, and most preferably contains no oxygen. Most preferably the atmosphere comprising hydrogen contains no oxygen for two reasons: firstly, to mitigate any pyrophoric activity of the at least one element from groups 7, 8, 9, 10 and 11 of the periodic table on the carbon support as it/they begin to get reduced, and secondly, to avoid the creation of an explosive hydrogen-oxygen mixture. Limits of an explosive hydrogen-oxygen mixture from literature are as follows: a lower explosion limit at 3.4 mol % hydrogen in air, and a higher explosion limit at 77.6 mol % hydrogen in air at 100° C.

Suitably, the atmosphere comprising hydrogen may contain at least some amount of inert gases such as nitrogen, helium or argon, as the presence of these gases may aid in the control of the reduction rate during the catalyst activation step. Preferably, the atmosphere comprising hydrogen may comprise 10 parts inert gas to 1 part hydrogen gas, or more preferably 100 parts inert gas to 1 part hydrogen gas. The latter may be more suitable if any structural change to the at least one element from groups 7, 8, 9, 10 and 11 of the periodic table undergoing activation is to be avoided.

To create an atmosphere comprising hydrogen in the reactor vessel, after placing the dried metal impregnated carbon in the reactor vessel, the reactor vessel is sealed and suitably it gaseous content replaced by an inert gas, such as nitrogen, helium or argon, by at least one round of loading the reactor vessel with the inert gas, followed by the evacuation of such inert gas and replacing it with the atmosphere comprising hydrogen to be used for the reduction process. Preferably, only the atmosphere comprising hydrogen is then present in the inert gas-flushed reactor vessel, which remains sealed.

The catalyst activation step is started suitably by supplying the reactor vessel with the atmosphere comprising hydrogen described herein, and suitably by raising the temperature inside the reactor vessel.

Preferably the total pressure inside the reactor vessel, which remains sealed for the catalyst activation step, is similar to, if not identical to, atmospheric pressure. Suitably the pressure may be at least 0.1 MPa and suitably need not be higher than 0.3 MPa. However, the use of a higher pressure, such as up to 20 MPa, is not excluded if it is decided to carry out the catalyst activation step simultaneously with the start of the running of the glycol production process of the present invention.

Suitably, the supply of an atmosphere comprising hydrogen into the sealed reactor vessel may be continuous, which enables the removal from the reactor vessel of any water or other components that may be generated during the catalyst activation step. Such removal suitably prevents undesired changes to the catalyst composition's structure (which might include, for example, uneven metal aggregation on the carbon support). For the avoidance of doubt, although the atmosphere comprising hydrogen can enter, flow through, and exit from the reactor vessel, the reactor vessel remains sealed such that its interior is not exposed to an oxygen containing atmosphere, such as air. Such is also the case during later steps when the reactor vessel is supplied with the saccharide-containing feedstock and hydrogen to carry out the production of glycols, and to remove the reaction products.

The supply of an atmosphere comprising hydrogen into the reactor vessel is followed by raising the temperature inside the reactor vessel to start and continue the catalyst activation step. Preferably, the catalyst activation step may be carried out at a temperature of at least 25° C., more preferably at a temperature of at least 160° C., even more preferably at a temperature of at least 200° C., and most preferably at a temperature of at least 230° C. Preferably, the catalyst activation step may be carried out at a temperature of at most 350° C., more preferably at a temperature of at most 325° C., even more preferably at a temperature of at most 305° C., and most preferably at a temperature of at most 285° C. The reactor vessel remains sealed throughout these steps, as discussed above. Preferably the catalyst activation step is carried out at a temperature which is above the preferred reaction temperature of the hydrogenation step of the glycol production process described herein. A suitable temperature range may also be in the range of from 305° C. to 350° C., or from 25° C. to 95° C.

The duration of the catalyst activation step is preferably at least 10 minutes, more preferably at least 1 hour, and even more preferably at least 2 hours. Suitably, the catalyst activation step may be carried out at 305° C. for 1 hour, however factors such as the activation temperature of choice and the hydrogen level of the atmosphere comprising hydrogen may affect the actual duration of the catalyst activation step.

At the end of the catalyst activation step an activated catalyst composition is formed, which is ready for use for the conversion of a saccharide-containing feedstock into glycols, but is not taken out of the sealed reactor vessel, or exposed to an oxygen containing atmosphere, such as air.

An advantage of the process for the preparation of the catalyst composition according to the present invention is that the prepared catalyst composition remains in the reactor vessel following its preparation and activation, ready for use in, for example, the glycol preparation process from saccharide-containing feedstock as described herein. Normally when hydrogen reduction is carried out to activate supported catalysts, the resultant metal particles can become pyrophoric in the presence of oxygen. As the catalyst composition prepared according to the invention remains in the reactor vessel following its preparation, it is not exposed to detrimental levels of oxygen, and therefore such pyrophoric behaviour becomes irrelevant. Further, as the glycol preparation process according to the present invention takes place in the presence of pure hydrogen, whilst using the process of the invention, the activated catalyst composition is not exposed to detrimental levels of oxygen. Therefore the advantages of the present invention include: (i) the reduction in the number steps comprising the activation process, as compared to the prior art, (ii) the minimisation of the complexity of the activation process, (iii) the amount of equipment, and its complexity, needed for the activation process is minimised; and (iv) a catalyst composition that is hydrothermally stable and active under the conditions of the continuous conversion of a saccharide-containing feedstock into glycols described herein.

As the glycol preparation process according to the present invention takes place in the presence of hydrogen, and preferably in the absence of air or oxygen, to commence the glycol preparation process according to the present invention, the vessel just needs to be supplied with the remaining components of the glycol preparation process, and the process conditions need to be adjusted as described below.

This is achieved by supplying to the reactor vessel a saccharide-containing feedstock, a retro-aldol catalyst composition and further hydrogen.

The present invention provides a process for the conversion of a saccharide-containing feedstock into glycols in the presence of the catalyst composition prepared according to the invention.

The glycols produced by the process of the present invention are preferably MEG, MPG and 1,2-BDO, and more preferably MEG and MPG, and most preferably MEG.

The saccharide-containing feedstock for the glycol production process of the present invention comprises starch. It may also comprise one or further saccharides selected from the group consisting of monosaccharides, disaccharides, oligosaccharides and polysaccharides. An example of a suitable monosaccharide is glucose, and an example of a suitable disaccharide is sucrose. Examples of suitable oligosaccharides and polysaccharides include cellulose, hemicelluloses, glycogen, chitin and mixtures thereof.

The saccharide-containing feedstock may be derived from grains such as corn, wheat, millet, oats, rye, sorghum, barley or buckwheat, from rice, from pulses such as soybean, pea, chickpea or lentil, from bananas and/or from root vegetables such as potato, yam, sweet potato, cassava and sugar beet, lignocellulosic materials such as but not limited to softwood, or any combinations thereof. A preferred source of saccharide-containing feedstock is corn.

A pre-treatment step may be applied to the saccharide-containing feedstock to remove particulates and other unwanted insoluble matter, or to render the carbohydrates accessible for hydrolysis and/or other intended conversions. After the pre-treatment, the treated feedstock stream is suitably converted into a solution, a suspension or a slurry in a solvent.

The solvent may be water, or a $C_1$ to $C_6$ alcohol or polyalcohol, or mixtures thereof. Suitably $C_1$ to $C_6$ alcohols include methanol, ethanol, 1-propanol and isopropanol. Suitably polyalcohols include glycols, particularly products of the hydrogenation reaction, glycerol, erythritol, threitol, sorbitol, 1,2-hexanediol and mixtures thereof. More suitably, the poly alcohol may be glycerol or 1,2-hexanediol. Preferably, the solvent comprises water. The solvent may also include the recycled heavies, or components thereof (e.g. glycerol), formed during the glycol process.

The concentration of the saccharide-containing feedstock as a solution or slurry in the solvent supplied to the reactor vessel is at most at 80% wt., more preferably at most at 60% wt. and more preferably at most at 45% wt. The concentration of the saccharide-containing feedstock as a solution in the solvent supplied to the reactor vessel is at least 5% wt., preferably at least 20% wt. and more preferably at least 35% wt.

The glycol preparation process according to the present invention takes place in the presence of hydrogen. Preferably, the process takes place in the absence of air or oxygen. As the catalyst composition preparation step is also carried out in the absence of oxygen, following such activation the reactor is ready to receive the components of the glycol preparation process. Therefore, as well as the saccharide-containing feedstock, a retro-aldol catalyst composition and further hydrogen are supplied to the reactor vessel, and the process conditions are adjusted as described below.

Preferably, the active catalytic components of the catalyst component with retro-aldol catalytic capabilities comprises of one or more compound, complex or elemental material comprising tungsten, molybdenum, vanadium, niobium, chromium, titanium, zirconium or tin. More preferably the active catalytic components of the catalyst component with retro-aldol catalytic capabilities comprises of one or more material selected from the list consisting of tungstic acid, molybdic acid, ammonium tungstate, ammonium metatungstate, ammonium paratungstate, sodium phosphotungstate, sodium metatungstate, tungstate compounds comprising at least one Group I or II element, metatungstate compounds comprising at least one Group I or II element, paratungstate compounds comprising at least one Group I or II element, phosphotungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulphate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the catalyst component with retro-aldol catalytic capabilities comprises one or more compound, complex or elemental material selected from those containing tungsten or molybdenum.

In one embodiment, the active catalytic components of the catalyst component with retro-aldol catalytic capabilities is supported on a solid support, and operates as a heterogeneous catalyst. The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In another embodiment, the active catalytic component of the catalyst component with retro-aldol catalytic capabilities is unsupported, and operates as a homogeneous catalyst. Preferably, in this embodiment the active catalytic components of the catalyst component with retro-aldol catalytic capabilities is metatungstate, which is delivered into the reactor vessel as an aqueous solution of sodium metatungstate.

Suitable reactor vessels that can be used in the process of the preparation of glycols from a saccharide-containing feedstock include continuous stirred tank reactors (CSTR), plug-flow reactors, slurry reactors, ebullated bed reactors, jet flow reactors, mechanically agitated reactors, bubble columns, such as slurry bubble columns and external recycle loop reactors. The use of these reactor vessels allows dilution of the reaction mixture to an extent that provides high degrees of selectivity to the desired glycol product (mainly ethylene and propylene glycols).

The process for the hydrogenation or hydrogenolysis of a saccharide-containing feedstock takes place in a reactor. The temperature in the reactor is suitably at least 80° C., preferably at least 130° C., more preferably at least 160° C., most preferably at least 190° C. The temperature in the reactor is suitably at most 300° C., preferably at most 280° C., more preferably at most 250° C., most preferably at most 230° C. Operating at higher temperatures has the potential disadvantage of increased amounts of side-reactions, leading to lower yield, and operating at a low temperature might result in suppression or inactivation of the retro-aldol activity.

The pressure in the reactor is suitably at least 1 MPa, preferably at least 2 MPa, more preferably at least 3 MPa. The pressure in the reactor is suitably at most 25 MPa, preferably at most 20 MPa, more preferably at most 18 MPa. Preferably, the reactor is pressurised to a pressure within these limits by addition of hydrogen before addition of any reactant or water and is maintained at such a pressure as the reaction proceeds through on-going addition of hydrogen.

The residence time in the reactor is suitably at least 1 minute, preferably at least 2 minutes, more preferably at least 5 minutes. Suitably the residence time in the reactor is no more than 5 hours, preferably no more than 2 hours, more preferably no more than 1 hour.

The present invention is further illustrated in the following Examples.

The experiments were conducted in a Hastelloy (C22) autoclave of 100 ml total volume (50 ml liquid hold-up), which was loaded with 0.5 g of the metal impregnated carbon, impregnated with 1.2% wt. ruthenium with respect to the total weight of the resultant catalyst. The catalyst precursor solution comprised ruthenium nitrosyl nitrate.

The metal impregnated carbon did not undergo any other treatments after impregnation with the catalyst precursor solution comprising ruthenium, except for drying overnight at 80° C.

The autoclave was sealed and the metal impregnated carbon was activated by treating it for 1 hour at 300° C. under a continuous stream of an atmosphere comprising hydrogen, at a rate of 9 L/hour at standard temperature and pressure (STP). The atmosphere comprising hydrogen in this instance was pure hydrogen which did not contain any inert gas. Maintaining a continuous stream of the atmosphere comprising hydrogen served to remove any moisture and any other components that may have formed during the activation step and served to prevent the formation of ruthenium metal aggregation on the carbon support.

After the activation by reduction was completed, water was fed to the reactor via two separate feed lines at a rate of 30 g/hour per feed line, at reaction conditions until conditions in the reactor vessel reached steady state operational conditions, such as gas and liquid flow rates, temperature and pressure.

In particular, the saccharide-containing feedstock into glycols conversion reaction temperature was set to 230° C. and total reactor vessel pressure was maintained at 10 MPa. Under such conditions, the gas phase comprising hydrogen and water was in equilibrium with the liquid phase.

Hydrogen gas was fed to the reactor vessel at 3 L/hour STP.

After stabilization with respect to gas and liquid flow rates, the reactor vessel temperature and pressure, both feeds were switched simultaneously from water to the reaction feeds, being: (i) an aqueous solution of 2000 ppmwt sodium metatungstate and 900 ppmwt sodium bicarbonate were fed to the reactor at a rate of 30 g/hour via a first feed line; and simultaneously, a 2 wt % glucose solution in water (saccharide-containing feedstock) to the reactor at a rate of 30 g/hour via a second feed line.

The total reactor feed of 1 wt % glucose, 1000 ppmwt. sodium metatungstate, and 450 ppmwt. sodium bicarbonate was fed to the reactor vessel at a rate of 60 g/hr.

Residence time in the reactor was 50 minutes.

The pH of the cooled reactor vessel effluent was in the range of 4.2 to 4.5.

Results & Discussions

The product composition of the reactor effluent were analysed by GC and by HPLC.

Product yields are shown in FIG. 1 and are tabulated in more detail in Table 1.

Using the catalyst composition treated as described above, after a 30-hour induction period, the MEG yield levelled to around 55-60%, with the total glycols yield (MEG+MPG+1,2-butanediol (1,2-BDO)) being at around 60-65%. Sorbitol yields were low (~3%) and gradually decreased over time.

Hydroxyactone (HA) and 1-hydroxy-2-butanone (1H2BO) yields were relatively stable during the entire run, with yields in the range of 0.3% and 0.1% respectively.

The erythritol/Threitol yields increased significantly at the end of the run.

Hardly any carboxylic acids were observed (~0.1% total yield). The reaction was stopped after 114 hrs runtime. The product was colourless during the entire run.

The spent catalyst composition was recovered and submitted together with a fresh reference sample for TEM/EDS.

Analysis revealed that the average Ru loading of the fresh and spent catalyst composition was similar (1.05 vs. 1.18 wt % Ru), indicating that Ru leaching was not an issue.

The catalyst composition that was prepared, and reduced according to the process of the present invention, proved to be an active hydrogenation catalyst under the conditions of the continuous conversion of a saccharide-containing feedstock into glycols described herein.

TABLE 1

Product yields (mass of product obtained related to the mass of saccharide feedstock intake).

| Run time (h) | MEG | MPG | 1,2-BDO | Sorbitol | Erythritol and Threitol | Glycerol | Total glycols* | Glucose conver-sion (%) |
|---|---|---|---|---|---|---|---|---|
| | | | | Yield (%) | | | | |
| 29 | 56.9 | 4.8 | 1.2 | 3.2 | 4.9 | 2.6 | 62.9 | 99.7 |
| 68 | 56.4 | 4.7 | 1.3 | 2.4 | 4.9 | 2.2 | 62.4 | 99.9+ |
| 114 | 57.2 | 5.1 | 1.4 | 1.5 | 13.1 | 1.8 | 63.7 | 99.9+ |

That which is claimed is:

1. A process for the production of glycols comprising the step of:
    (a) contacting a carbon support with a catalyst precursor solution comprising at least one element from groups 7, 8, 9, 10 and 11 of the periodic table to form a metal impregnated carbon;
    (b) drying the metal impregnated carbon at a temperature of no greater than 400° C. and placing in a reactor vessel;
    (c) sealing the reactor vessel;
    (d) treating the metal impregnated carbon in the sealed reactor vessel in an atmosphere comprising hydrogen at a temperature of from 25° C. to 350° C. to form an activated catalyst composition;
    (e) whilst the catalyst composition remains inside the reactor vessel in an atmosphere comprising hydrogen, supplying to the reactor vessel a saccharide-containing feedstock, a retro-aldol catalyst composition, a solvent and further hydrogen.

2. The process claimed in claim 1, wherein the glycols comprise ethylene glycol and 1, 2-propylene glycol.

3. The process claimed in claim 1, wherein the saccharide-containing feedstock comprises one or more saccharide selected from the group consisting of monosaccharides, disaccharides, oligosaccharides and polysaccharides.

4. The process claimed in claim 1, wherein the retro-aldol catalyst composition comprises tungsten.

5. The process claimed in claim 1, wherein the process is carried out at a temperature of from 80° C. to 300° C.

6. The process claimed in claim 1, wherein catalyst precursor solution comprises ions of at least one element selected from a group consisting of ruthenium, cobalt, nickel, palladium, platinum, iridium, rhenium and copper.

7. The process claimed in claim 1, wherein the catalyst precursor solution comprises water.

8. The process claimed in claim 1, wherein the catalyst precursor solution comprises an alcohol or acetone.

\* \* \* \* \*